United States Patent [19]

Johnson et al.

[11] 4,110,532

[45] Aug. 29, 1978

[54] 5-HYDROXY-PGI₁ COMPOUNDS

[75] Inventors: Roy A. Johnson; John C. Sih, both of Kalamazoo, Mich.

[73] Assignee: The Upjohn Company, Kalamazoo, Mich.

[21] Appl. No.: 815,648

[22] Filed: Jul. 14, 1977

[51] Int. Cl.² .......................................... C07D 307/93
[52] U.S. Cl. ................................ 542/426; 542/421; 542/422; 542/429; 260/343.21; 260/343.5; 260/346.22; 260/346.73
[58] Field of Search ...................... 260/346.22, 346.73, 260/343.21, 343.5; 542/421, 422, 426, 429

[56] References Cited

PUBLICATIONS

Johnson et al., Prostaglandins 12, 915 (1976).

*Primary Examiner*—Henry R. Jiles
*Assistant Examiner*—Bernard Dentz
*Attorney, Agent, or Firm*—Robert A. Armitage

[57] ABSTRACT

This invention relates to certain structural analogs of 5,6-dihydroprostacyclin (PGI₁) wherein the C-5 carbon atom is substituted by hydroxy. These novel 5-hydroxyprostacyclin-type compounds are smooth muscle stimulators.

53 Claims, No Drawings

5-HYDROXY-PGI₁ COMPOUNDS

BACKGROUND OF THE INVENTION

This invention relates to novel structural analogs of 5,6-dihydroprostacyclin (PGI₁). In particular, the present invention relates to prostacyclin-type compounds wherein the C-5 carbon atom of 5,6-dihydroprostacyclin is substituted by a hydroxy.

Prostacyclin (PGI₂) is an endogenously produced compound in mammalian species, being structurally and bio-synthetically related to the prostaglandins (PG's). In particular, prostacyclin exhibits the following structure and atom numbering:

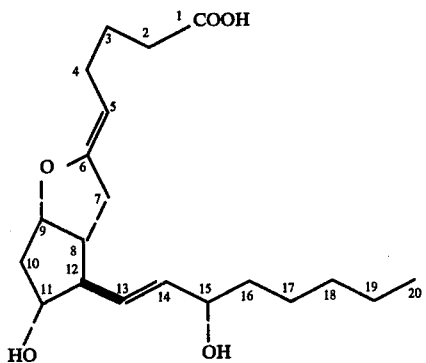

Similarly, 5,6-dihydroprostacyclin exhibits the following structure and atom numbering:

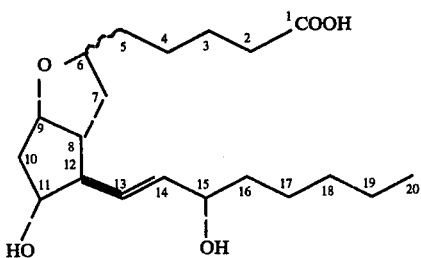

As is apparent from inspection of formulas I and II, prostacyclin and 5,6-dihydroprostacyclin bear a structural relationship to PGF₂α, which exhibits the following structure and atom numbering:

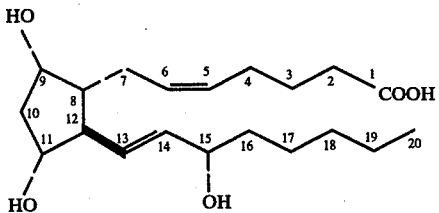

As is apparent by reference to formula III, prostacyclin may be trivially named as a derivative of PGF-type compounds. Accordingly, prostacyclin is trivially named 9-deoxy-6,9α-epoxy-5Z)-5,6-didehydro-PGF₁. Likewise, 5,6-dihydroprostacyclin is named as (6S)- or (6R)-9-deoxy-6,9α-epoxy-PGF₁. For description of the geometric isomerism employed above, see Blackwood et al., Journal of the American Chemical Society 90, 509 (1968). The stereoisomerism above is determined by the Cahn-Ingold-Prelog sequence rules. See J. Chem. Ed. 41:16 (1964). Further, for a description of prostacyclin and its structural identification, see Johnson et al., Prostaglandins 12, 915 (1976).

For convenience, the novel prostacyclin analogs described herein will be referred to by the trivial, art-recognized system of nomenclature described by N. A. Nelson, Journal of Medicinal Chemistry 17:911 (1974) for the prostaglandins. Accordingly, all of the novel prostacyclin derivatives herein will be named as 9-deoxy-PGF₁-type compounds.

In formulas I, II and III above, as well as in formulas hereinafter, broken line attachments to any ring indicate substituents in "alpha" (α) configuration, i.e., below the plane of such ring. Heavy solid line attachments to any ring indicate substituents in "beta" (β) configuration, i.e., above the plane of such ring. The use of wavy lines (~) herein will represent attachment of substituents in either the alpha or beta configuration or attachment in a mixture of alpha or beta configurations.

The side-chain hydroxy at C-15 in the above formulas is in S or R configuration, as determined by the Cahn-Ingold-Prelog sequence rules. See J. Chem. Ed. 41:16 (1964). See also Nature 212, 38 (1966) for discussion of the stereochemistry of the prostaglandins, which discussion applies to the novel prostacyclin analogs herein. Expressions such as C-5, C-15, and the like refer to the carbon atom in the prostaglandin or prostacyclin analog which is in the position corresponding to the position of the same number in PGF₂α or prostacyclin, as enumerated above.

Molecules of prostacyclin and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the above formula for prostacyclin corresponds to that endogenously produced in mammalian tissues. In particular, refer to the stereoconfiguration at C-8 (alpha), C-9 (alpha), C-11 (alpha), and C-12 (beta) of endogenously-produced prostacyclin. The mirror image of the above formula for prostacyclin represents the other enantiomer. The racemic forms of prostacyclin contains equal numbers of both enantiomeric molecules, and the above formula I and its mirror image is needed to represent correctly the corresponding racemic prostacyclin.

For convenience hereinafter, use of the term prostaglandin ("PG") or prostacyclin ("PGI₂") will mean the optically active form of that prostaglandin or prostacyclin thereby referred to with the same absolute configuration as PGF₂α, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one of the same pharmacological purposes as the prostaglandins or prostacyclin, respectively.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostacyclin analog," as used herein, represents that stereoisomer of a prostacyclin-type product which is of the same relative stereochemical configuration as prostacyclin obtained from mammalian tissues or a mixture comprising that stereoisomer and the enantiomer thereof. In particular, where a formula is used to depict a prostacyclin-type product herein, the term "prostacyclin analog" refers to the compound of that formula or a mixture comprising that compound and the enantiomer thereof.

SUMMARY OF THE INVENTION

The present invention particularly comprises:
A prostacyclin analog of the formula

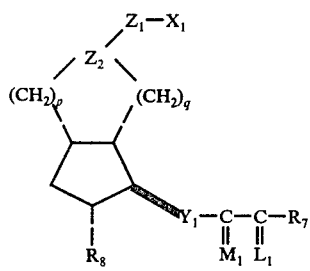

IV wherein $R_7$ is (1) —$(CH_2)_m$—$CH_3$, (2) —$(CH_2)_h$⟨⟩—$(T)_s$, or (3) —O—⟨⟩—$(T)_s$ wherein $R_7$ is (1) —$(CH_2)_m$—$CH_3$, (2) —$(CH_2)_h$⟨⟩—$(T)_s$, or (3) —O—⟨⟩—$(T)_s$ wherein $m$ is 3; $h$ is the integer zero or one; $s$ is the integer zero, one, 2, or 3, and T is chloro, fluoro, trifluoromethyl, alkyl of one to 3 carbon atoms, inclusive, or with the proviso that not more than two T's are other than alkyl;

wherein $Z_2$ is

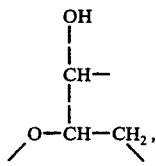 (1)

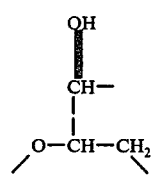 (2)

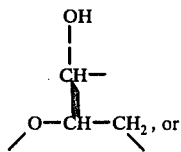 (3)

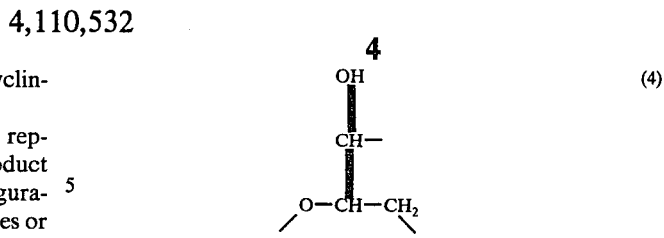 (4)

wherein one of $p$ or $q$ is the integer zero or one and the other is the integer zero;

wherein $Z_1$ is (1) —$(CH_2)_g$—$CH_2$—$CH_2$—, (2) —$(CH_2)_g$—$CH_2$—$CF_2$—, or (3) trans—$(CH_2)_g$—$CH$=$CH$—, wherein $g$ is the integer one, 2, or 3 when $q$ is zero and zero, one, or 2 when $q$ is one;

wherein $R_8$ is hydrogen, hydroxy, or hydroxymethyl;

wherein $Y_1$ is (1) trans—$CH$=$CH$—, (2) cis—$CH$=$CH$—, (3) —$CH_2CH_2$—, (4) trans—$CH$=$C(Hal)$—, or (5) —$C$≡$C$— wherein Hal is chloro or bromo;

wherein $M_1$ is

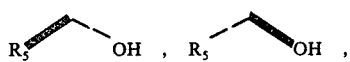

wherein $R_5$ is hydrogen or alkyl with one to 4 carbon atoms, inclusive;

wherein $L_1$ is

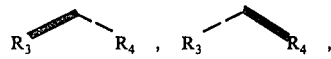

a mixture of

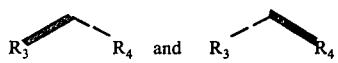

wherein $R_3$ and $R_4$ are hydrogen, methyl, or fluoro, being the same or different, with the proviso that one of $R_3$ and $R_4$ is fluoro only when the other is hydrogen or fluoro;

wherein $X_1$ is (1) —$COOR_1$; wherein $R_1$ is hydrogen, alkyl of one to 12 carbon toms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, (2) —$CH_2OH$, (3) —$CH_2NL_2L_3$, wherein $L_2$ and $L_3$ are hydrogen, alkyl of one to 4 carbon atoms, inclusive, or —$COOR_1$, wherein $R_1$ is as defined above;

(4) —$COL_4$, wherein $L_4$ is (a) amino of the formula —$NR_{21}R_{22}$, wherein $R_{21}$ and $R_{22}$ are hydrogen, alkyl of one to 12 carbon atoms, inclusive; aralkyl or 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;

(b) cycloamino selected from the group consisting of

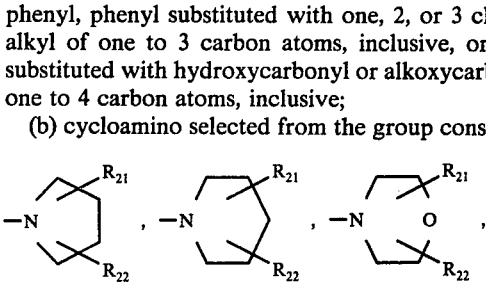

-continued

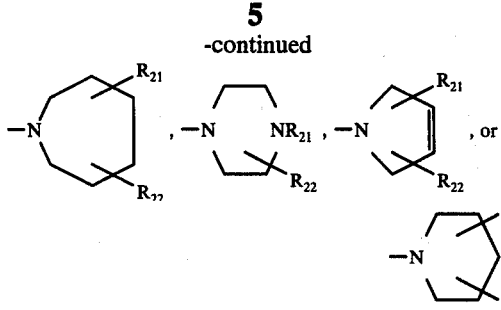

wherein R$_{21}$ and R$_{22}$ are as defined above;

(c) carbonylamino of the formula —NR$_{23}$COR$_{21}$, wherein R$_{23}$ is hydrogen or alkyl of one to 4 carbon atoms and R$_{21}$ is as defined above;

(d) sulfonylamino of the formula —NR$_{23}$SO$_2$R$_{21}$, wherein R$_{21}$ and R$_{23}$ are as defined above; or (5) —COOL$_5$, wherein L$_5$ is p-substituted phenyl selected from the group consisting of

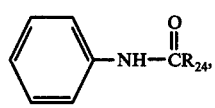

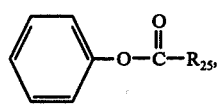

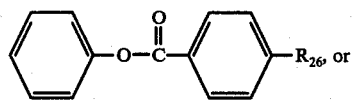

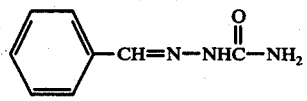

wherein R$_{24}$ is methyl, phenyl, acetamidophenyl, benzamidophenyl, or —NH$_2$; R$_{25}$ is methyl, phenyl, —NH$_2$, or methoxy; and R$_{26}$ is hydrogen or acetamido; and the 1,5- and 1,15-lactones thereof.

For convenience, the novel prostacyclin analogs described above will be referred to by the trivial, art-recognized system of nomenclature described by N. A. Nelson, Journal of Medicinal Chemistry 17:911 (1974). However, for added convenience both names derivated from PGF$_1$ and PGI will be optionally and interchangeably used hereinafter. Accordingly, 9-deoxy-6,9α-epoxy-5-hydroxy-16-phenyl-17,18,19,20-tetranor-PGF$_1$, methyl ester is represented by formula IV, above, when X$_1$ is —COOCH$_3$, Z$_1$ is —(CH$_2$)$_3$—, Y$_1$ is trans-CH=CH—, R$_3$, R$_4$, and R$_5$ are all hydrogen and the hydroxy of the M$_1$ moiety is in the alpha configuration, p an q are zero, and R$_7$ is phenyl. The C-15 epimer of the compound named above (15-epi-9-deoxy-6,9α-epoxy-5-hydroxy-16-phenyl-17,18,19,20-tetranor-PGF$_2$, methyl ester) is represented above when the hydroxy of the M$_1$ moiety is in the beta configuration. Optionally these compounds are named as 5-hydroxy-16-phenyl-18,19,20-trinor-PGI, methyl ester and its 15-epimer.

The side-chain hydroxy at C-15 in the above formulas is in S or R configuration, as determined by the Cahn-Ingold-Prelog sequence rules. See J. Chem. Ed. 41:16 (1964). See, also, Nature 212, 28 (1966) for discussion of the stereochemistry of the prostaglandins. See particularly U.S. Ser. No. 6282,848 for description of the various conventions with respect to the stereochemistry at C-15 as employed herein.

Finally, the NOMENCLATURE TABLE herein describes the convention by which trivial names are further assigned for the novel compounds herein:

NOMENCLATURE TABLE

| Z$_2$ | p | q | Compound Type |
|---|---|---|---|
| (1) OH │ CH— │ O—CH—CH$_2$ | 0 | 0 | (5R,6S)-9-deoxy-6,9α-epoxy-5-hydroxy-PGF$_1$-type compounds |
| | 0 | 1 | (4R,5S)-9-deoxy-5,9α-epoxy-4-hydroxy-PGF$_1$-type compounds |
| | 1 | 0 | (5R,6S)-9-deoxy-6,9α-epoxy-methylene-5-hydroxy-PGF$_1$-type compounds |
| (2) OH │ CH— │ O—CH—CH$_2$ | 0 | 0 | (5S,6S)-9-deoxy-6,9α-epoxy-5-hydroxy-PGF$_1$-type compounds |
| | 0 | 1 | (4S,5S)-9-deoxy-5,9α-epoxy-4-hydroxy-PGF$_1$-type compounds |
| | 1 | 0 | (5S,6S)-9-deoxy-5-epoxy-methylene-5-hydroxy-PGF$_1$-type compounds |
| (3) OH │ CH— │ O—CH—CH$_2$ | 0 | 0 | (5R,6R)-9-deoxy-6,9α-epoxy-5-hydroxy-PGF$_1$-type compounds |
| | 0 | 1 | (4R,5R)-9-deoxy-5,9α-epoxy-4-hydroxy-PGF$_1$-type compounds |
| | 1 | 0 | (5R,6R)-9-deoxy-6,9α-epoxy-methylene-5-hydroxy-PGF$_1$-type compounds |
| (4) OH │ CH— │ O—CH—CH$_2$ | 0 | 0 | (5S,6R)-9-deoxy-6,9α-epoxy-5-hydroxy-PGF$_1$-type compounds |
| | 0 | 1 | (4S,5R)-9-deoxy-5,9α-epoxy-4-hydroxy-PGF$_1$-type compounds |
| | 1 | 0 | (5S,6R)-9-deoxy-5-epoxy-methylene-5-hydroxy-PGF$_1$-type compounds |

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-napthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4- chloro-2-methylphenyl, and 2,4-dichloro-3-methylphenyl,

Examples of

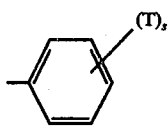

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)-ethylphenyl, 2-ethyl-p-tolyl, 4-ethyl-o-tolyl, 5-ethyl-m-tolyl, (o-, m- or p-)propylphenyl, 2-propyl(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-(di-fluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, o-, m-, or p-trifluoromethylphenyl, (o-, m-, or p-)methoxyphenyl, (o-, m-, or p-) ethoxyphenyl, (4-or 5-)chloro-2-methoxyphenyl, and 2,4-dichloro(5- or 6-)methylphenyl.

Amides within the scope of amino groups of the formula —$NR_{21}R_{22}$ are the unsubstituted amide (—$NH_2$), methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Still further examples are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Still further examples are benzylamide, 2-phenylethylamide, N-methyl-N-benzylamide, and dibenzylamide. Still further examples are anilide, p-chloroanilide, m-chloroanilide, 2,4-dichloroanilide, 2,4,6-trichloroanilide, p-methylanilide, m-methylanilide, and p-methoxycarbonylanilide.

Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

Amides within the scope of carbonylamino of the formula —$NR_{23}COR_{21}$ are methylcarbonylamide, ethylcarbonylamide, phenylcarbonylamide, and benzylcarbonylamide. Amides within the scope of sulfonylamido of the formula —$NR_{23}SO_2R_{21}$ are methylsulfonylamide, ethylsulfonylamide, phenylsulfonylamide, p-tolylsulfonylamide, and benzylsulfonylamide.

Substituted phenyl esters within the scope of the p-substituted phenyl groups described above are p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

The novel prostacyclin analogs of this invention correspond to the naturally occurring prostaglandins in that the novel prostacyclin analogs are capable of stimulating smooth muscle (as shown by tests, for example, on the gerbil colon).

Because of this biological response, these novel PG analogs are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The novel prostacyclin analogs are also highly active in potentiating other known smooth muscle stimulators, for example, oxytocic agents, e.g., oxytocin, and the various ergot alkaloids including derivatives and analogs thereof. Therefore, these compounds, for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the novel prostaglandin analog is administered by intravenous infusion immediately after abortion or delivery at a dose in the range about 0.01 to about 50 μg per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

Another aspect of the use of the novel prostacyclin analogs of this invention, especially the preferred PG analogs defined hereinbelow, is that these novel prostacyclin analogs are administered effectively orally, sublingually, intravaginally, buccally, or rectally, in addition to the intravenous, intramuscular, or subcutaneous injection or infusion methods of administration. These alternate routes of administration are advantageous because they facilitate maintaining uniform levels of these compounds in the body with fewer, shorter, or smaller doses and make possible self-administration by the patient.

Accordingly, the novel prostacyclin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For that purpose, it is preferred because of increased water solubility that when $X_1$ is —$COOR_1$, that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

When $X_1$ is —$COOR_1$, the novel prostacyclin analogs so described are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above arethose with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

To obtain the optimum combination of biological response specificity, potency, and duration of activity, certain novel prostacyclin analogs within the scope of this invention are preferred in that they exhibit increased potency, duration of selectivity of action, provide more easily stabilized pharmacological formulations, or exhibit a decreased toxicity at the appropriate therapeutic or prophylactic dose. Accordingly, the preferred compounds herein include those compounds wherein g is 3 or 1, most especially 1, are preferred.

In cases where increased pharmacological potency is desired, those compounds wherein the C-15 hydroxy is of the "alpha" configuration are especially preferred. With regard to the various substituents at C-15 and C-16, it is preferred that at least one of $R_3$, $R_4$, and $R_5$ be hydrogen. Further, in the event one of $R_3$ and $R_4$ is methyl or fluoro, it is preferred that $R_3$ and $R_4$ both be methyl or fluoro, respectively.

For those compounds herein where $Y_1$ is cis—CH=CH— or —C≡C—, those compounds wherein $R_3$, $R_4$, and $R_5$ are all hydrogen are preferred.

For the ω-aryl (i.e., where $R_7$ is aryl) compounds herein, preferred compounds are those wherein s is zero or one and T is chloro, fluoro, or trifluoromethyl.

Regarding the nature of the C-2 substitution for the novel carboxyamides disclosed herein, the preferred amino substituents are those wherein $R_{21}$ and $R_{22}$ are preferably hydrogen or alkyl of 1 to 8 carbon atoms, inclusive, being the same or different, preferably with the total number of carbon atoms in $R_{21}$ and $R_{22}$ being less than or equal to 8. More especially preferred are those carboxyamide substituents wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to four.

For convenience in preparation and use, the amino group $-NH_2$ is most especially preferred.

With regard to the various cycloamino groups described above, preferred cycloamino groups are those wherein the $R_{21}$ and $R_{22}$ substituents represent the preferred values therefore as described for the acyclic amido groups above. Most preferably, $R_{21}$ and $R_{22}$ are both hydrogen.

With regard to the carbonylamido groups described above, $R_{23}$ is preferably hydrogen and $R_{21}$ is preferably alkyl of one to 8 carbon atoms, inclusive. More preferably, $R_{21}$ is alkyl of one to 4 carbon atoms, inclusive, especially being methyl. Finally, with regard to the sulfonylamido groups described above, $R_{21}$ and $R_{23}$ most preferably exhibit those preferred values as described for carbonylamido groups.

Especially preferred are those compounds which satisfy two or more of the above preferences. Further, the above preferences are expressly intended to describe the preferred compounds within the scope of any generic formula of novel prostacyclin analogs disclosed herein. Thus, for example the above preferences describe preferred compounds within the scope of each formula of a prostacyclin analog provided herein.

The Charts herein described the methods whereby the novel prostaglandin analogs of this invention are prepared.

With respect to the Charts herein, $p$, $q$, $L_1$, $M_1$, $R_7$, $R_8$, $Y_1$, $Z_1$ and $Z_2$ are as defined above. $M_6$ is the acetal ether-derivatized form of $M_1$ wherein the hydroxyl group of the $M_1$ moiety is replaced by an acetal blocking group, herein referred to as $R_{10}$. $M_7$ is the silyl ether derivatized form of the $M_1$ moiety wherein the hydroxyl of $M_1$ is replaced by a silyl blocking group, $Si(G_1)_3$, especially t-butyldimethylsilyl. See U.S. Pat. No. 4,016,184 for further examples of such silyl groups. Likewise, $R_{36}$ and $R_{38}$ are the $R_{10}$-ether or $Si(G_1)_3$ ether derivatives, respectively, of $R_8$. In particular, acetal-type blocking groups such as tetrahydropyranyl and tetrahydrofuranyl are employed. See especially U.S. Pat. No. 4,016,184 for those groups contemplated for use herein. $X_3$ is —$COOR_1$ or —$COL_4$ wherein $R_1$ is an ester and $L_4$ is as defined above; —$NL_2L_3$, wherein $L_2$ and $L_3$ are as defined above; or CH—$OSi(G_1)_3$ or —CH$_2OR_{10}$, wherein —$Si(G_1)_3$ and $R_{10}$ are as defined above.

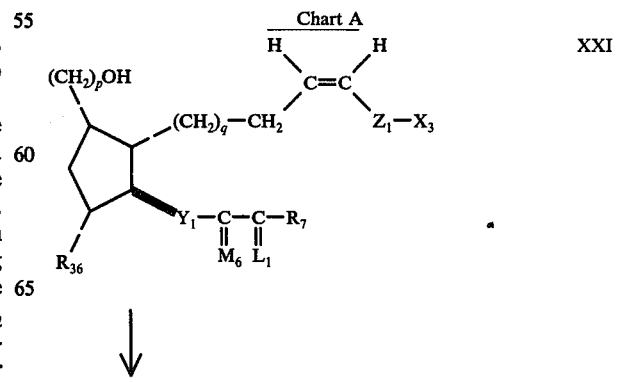

Chart A

-continued
Chart A
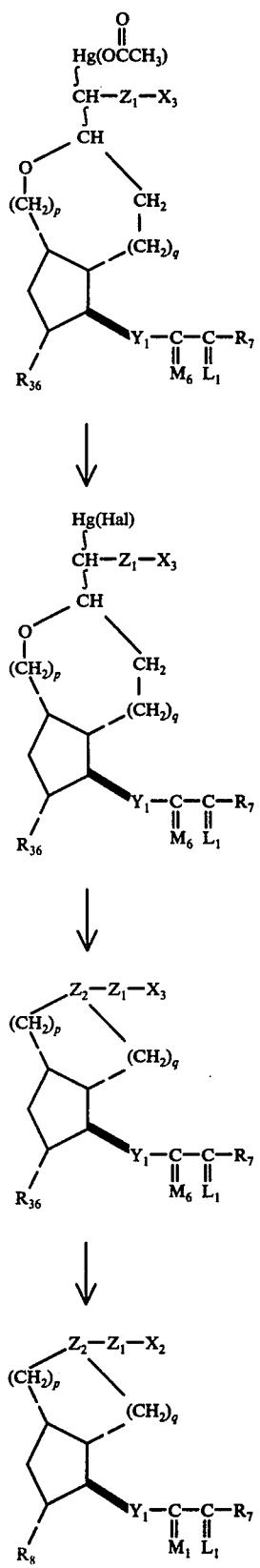
Chart B
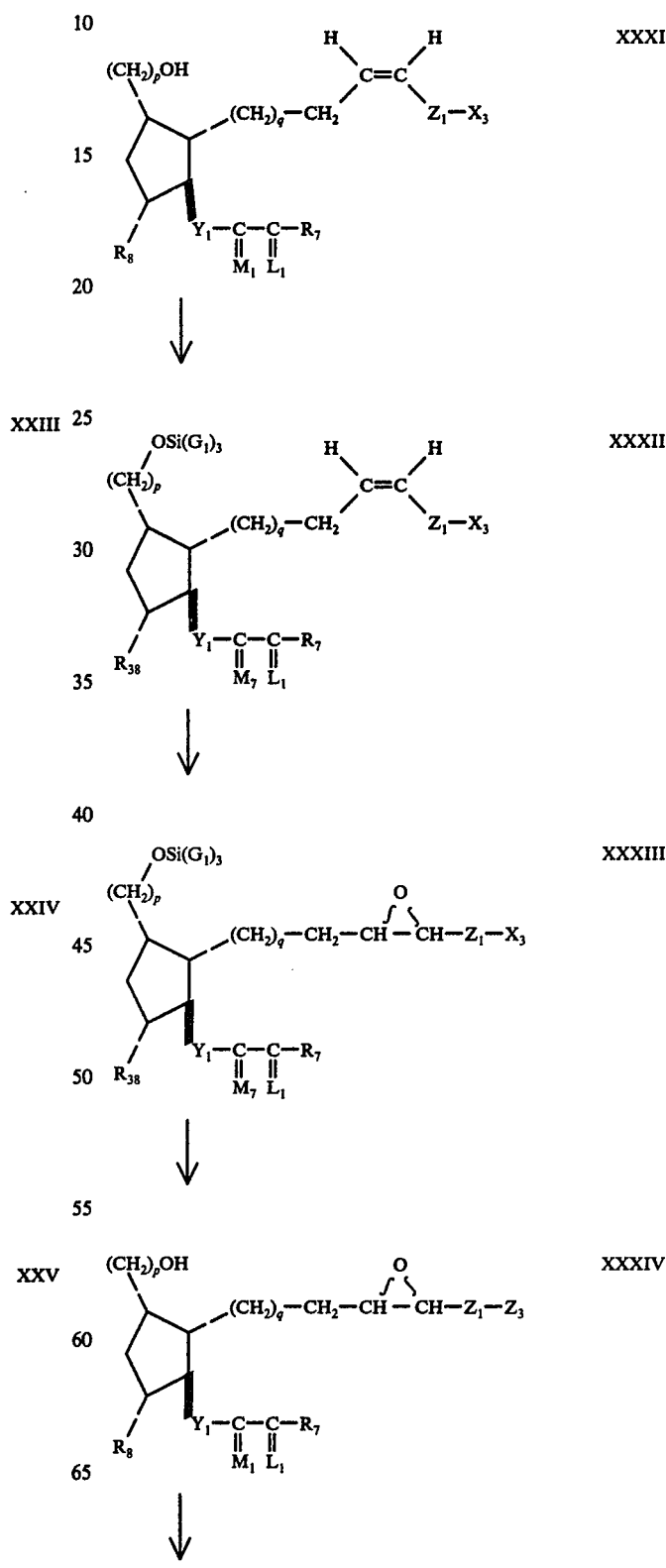

-continued
Chart B
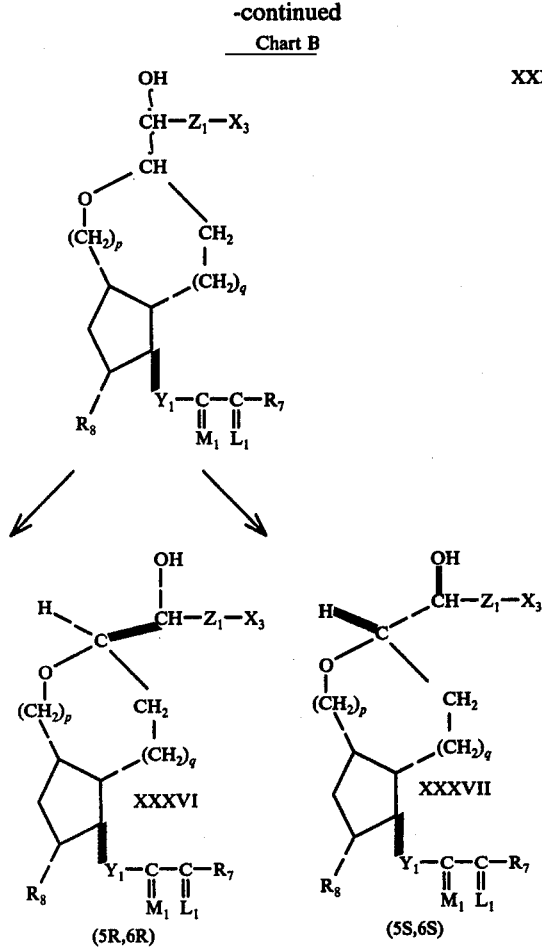
Chart C
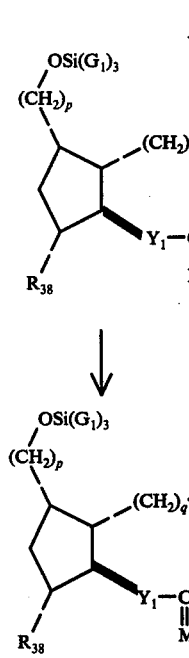
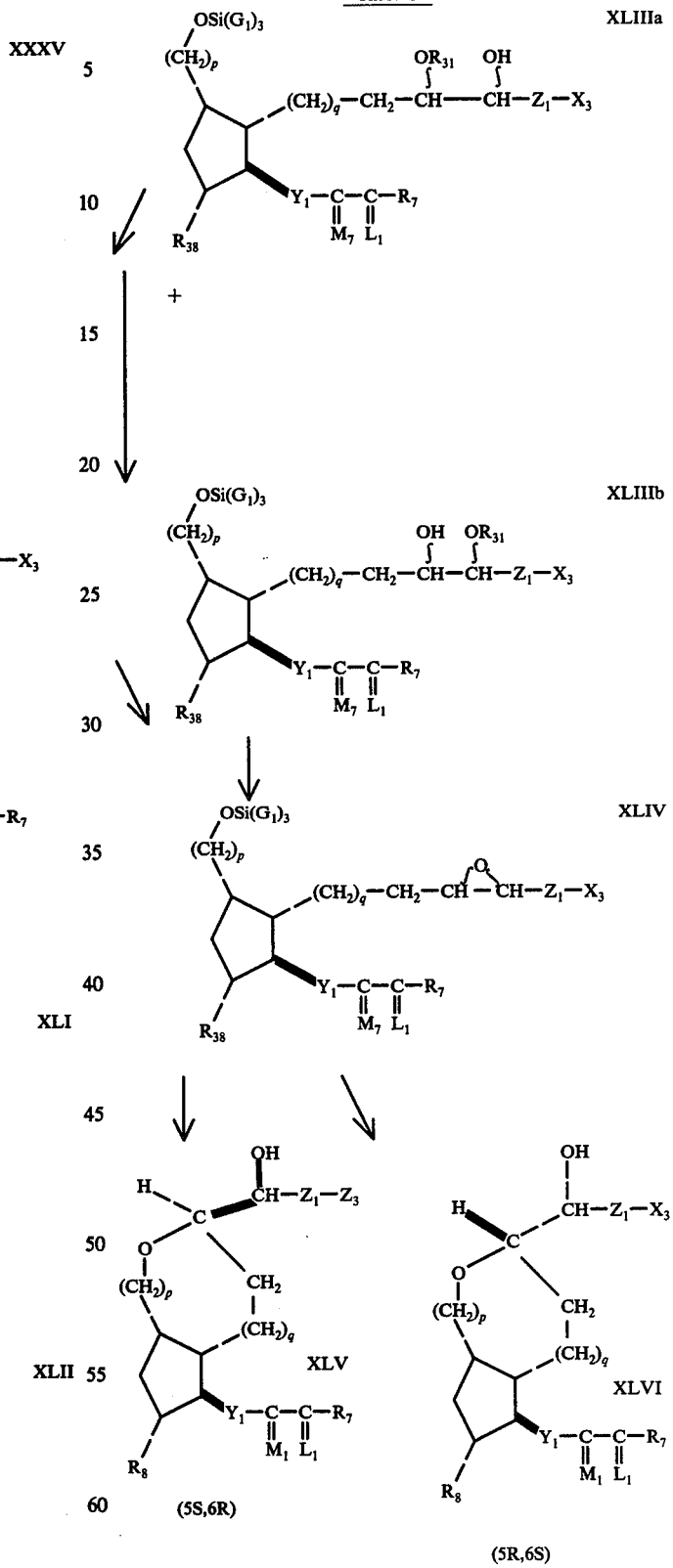
$R_{31}$ is an alkyl or aryl group such that the corresponding alkyl or aryl sulfonate represents a convenient and readily available moiety employed in the conventional replacement reaction as described in the Charts. For example, $R_{31}$ is preferably methyl or p-toluyl, such that the corresponding mesylate (methylsulfonate) or tosylate (p-toluenesulfonate) represents readily accessible derivatives of the hydroxyls.

Hal is chloro, bromo, or iodo.

With respect to Chart A, method is provided whereby the formula XXI PGF$_2\alpha$-type compound is transformed to the corresponding formula XXV prostacyclin analogs of the present invention.

With respect to formula XXI, these PGF$_2\alpha$ or cis-4,5-didehydro-PGF$_1\alpha$ compounds are known in the art or prepared by methods known in the art. For example, formula XXI acids are reduced to the corresponding alcohols or esterified by methods known in the art. Further, the formula XXI acids known in the art can be converted to the corresponding amides, e.g. using methods hereinafter, which amides are then reduced to the corresponding amines ($X_3$ is $-CH_2NL_2L_3$). Further, the various 11-deoxy and 11-deoxy-11-hydroxymethyl-PGF-type compounds of formula XXI are prepared by methods known in the art, as are the 9-deoxy-9$\alpha$-hydroxymethyl-PGF-type compounds of formula XXI.

The various formula XXI compounds are depicted therein as 11,15-bis(acetal)ethers. Such ethers are prepared by methods known in the art, particularly as described in U.S. Pat. No. 4,016,184.

Such ethers are prepared by etherifying the corresponding 11,15-dihydroxy or 15-hydroxy-PGF-type compounds or by known methods of prostaglandin total synthesis. See, for example, the total synthetic method described by U.S. Pat. No. 4,016,184, especially Chart K on columns 43 and 44 therein.

The formula XXII compound is thereafter prepared from the formula XXI compound by cyclizing and mercuroacetylating the formula XXI compound. This mercuroacetylation is accomplished by reacting the formula XXI compound with mercuric acetate, Hg(OAc)$_2$. Organic solvents such a tetrahydrofuran are employed in the transformation and reaction temperatures at or below ambient temperature are employed for convenience.

The formula XXIII compound is then transformed to the formula XXII compound by halo displacement of the acetate radical of the formula XXI compound. For this purpose, an aqueous solution of the sodium halide (e.g. sodium chloride or sodium bromide) corresponding to the formula XXIII halide to be prepared is employed. The reaction proceeds by stirring the sodium halide and the formula XXII compound together until thin layer chromatographic analysis indicates the reaction is complete.

Thereafter the formula XXIII compound is transformed to the formula XXIV compound by a reductive oxygenation. Accordingly, the formula XXIII compound is reacted with a reducing agent, preferably an alkali metal reducing agent (e.g., sodium borohydride), in the presence of molecular oxygen. When this reaction is complete, the formula XXIV compound is transformed to the prostacyclin analogs of the present invention by hydrolysis of any (acetal)ether blocking group. This hydrolysis proceeds by methods described in U.S. Pat. No. 4,016,184, particularly employing mixtures of water, tetrahydrofuran, and acetic acid.

With respect to the formula XXV compounds, each of the various isomers of the presen invention is obtained from the process of Chart A, the various isomers being separable by thin layer chromatographic means. For example, the two lesser polar and two more polar isomers of the formula XXIII isomeric mixture are conveniently separated prior to the reductive hydroxylation yielding the formula XXIV compounds. Thereupon the two formula XXIV isomeric pairs are separated into the four individual formula XXIV or formula XXV isomers, either before or after hydrolysis of the acetal-type blocking group.

By an optional, preferred procedure according to Chart A, the alcohols corresponding to the acetal ethers of formulas XXI-XXIV are employed in place of the ethers, thus obviating the need for the ether hydrolysis (i.e., the transformation XXIV to XXV) and yielding a formula XXV product directly from the formula XXIII intermediate. In accordance with this optical procedure, reference to formula XXI to XXII compounds shall mean reference to the alcohols corresponding thereto.

With respect to Chart B, a method is provided whereby the formula XXXI PGF$_2\alpha$- or cis-4,5-didehydro-PGF$_1\alpha$-type compounds are transformed to the corresponding formula XXXII (5R)-6$\beta$-PGI$_1$- and (5S)-6$\alpha$-PGI$_1$-type products of formulas XXXVI and XXXVII, respectively.

The transformation of the formula XXXI compound to the formula XXXII compound of Chart B is accomplished by silylation of each of the various hydroxyls of the formula XXXI compound. Methods of silylation are those described in U.S. Pat. No. 4,016,184. The formula XXXII silylated compound is then epoxidized to the corresponding formula XXIII 5$\alpha$, 6$\alpha$- or 5$\beta$, 6$\beta$-epoxy-PGF$_1\alpha$-type compound (q is 0) or 4$\alpha$, 5$\alpha$- or 4$\beta$, 5$\beta$-epoxy-PGF$_1\alpha$-type compound (q is 1) of formula XXXIII. This epoxidation proceeds by conventional methods for transformation of olefinic unsaturation to corresponding epoxide linkages, i.e., the use of peracids. For this purpose, m-chloroperbenzoic acid is employed. Conveniently, the epoxidation is accomplished by reacting one equivalent of the peracid with the formula XXXII compound in the presence of an inorganic base (e.g. sodium bicarbonate). Numerous organic solvents are employed in the transformation, particularly chlorinated hydrocarbons, and reaction temperatures from about $-20°$ C. to $10°$ C. are employed. Thereafter, the formula XXIII mixture of "cis" epoxides is transformed to the formula XXIV free hydroxy compound by selective hydrolysis of the silyl ethers. Accordingly, hydrolytic methods which preserve the epoxide linkage are employed. For this purpose an especially useful reagent is tetra-n-butyl-ammonium fluoride in tetrahydrofuran. See Corey et al., J.A.C.S. 94:6190 (1972) and U.S. Pat. No. 4,016,184 for a discussion of the selective hydrolysis employed in the present transformation.

Thereafter the formula XXXIV compound is transformed to the formula XXXV compound by cyclization. This cyclization is accomplished by first subjecting the formula XXXIV compound to neutral silica gel and thereafter combining the resulting product with acid-washed silica.

This formula XXXV isomeric mixture of products is then transformed to the formula XXXVI (5R)-6$\beta$-PGI$_1$-type product and formula XXXVII (5S)-6$\alpha$-PGI$_1$-type product.

Chart C provides and method whereby the formula XLI compound (see the formula XXXII compound of Chart B) is transformed to the two remaining isomers of the present invention: the formula XLV (5S)-6$\beta$-PGI$_1$-type compound and formula XLVI (5R)-6$\alpha$-PGI$_1$-type compound. By the procedure of Chart C, the formula XLI compound is first transformed to the corresponding formula XLII 5,6-glycol ($q$ is 0) or 4,5-glycol ($q$ is 1), employing conventional methods for glycol formation. For example, N-methylmorpholine-N-oxide dihydrate and osmium tetraoxide is combined with the formula XXI compound in an aqueous-alkanol solvent to yield the formula XLII compound. Reaction conditions at or about ambient temperature are maintained for several hours, until thin layer chromatographic analysis indicates the glycolization to be complete.

Thereafter, the formula XLII compound is transformed to one of the formula XLIII monoalkyl- or arylsulfonates, employing conventional methods for transforming hydroxyls to corresponding sulfonates. Accordingly, the sulfonyl chloride corresponding to the sulfonate to be prepared is reacted with the formula XLII compound in the presence of an amine (e.g. pyridine) at low temperatures (about −10° to 20° C.). About one equivalent of the sulfonyl chloride per equivalent of formula XLII compound is employed in order to assure formation of the monosulfonyl derivative.

The formula XLIV compound is then prepared from the formula XLIII(a) or formula XLIII(b) compound by reduction with sodium hydride, thereby eliminating the alkyl- or arylsulfonic acid. Reaction temperatures at −10° to 10° C. are employed and sodium hydride is added in the form of an oil dispersion. Organic solvents such as dimethylformamide are conveniently employed.

The formula XLIV epoxide thusly obtained is a "trans" epoxide, being a 5α,6β- or 5β,6α-epoxide when $q$ is 1 and a 4α,5β- or 4β,5α-epoxide when $q$ is 0. This trans epoxide is alternatively obtained by the procedure of Chart B from the 5,6-trans-PGF$_2$α-type or trans-4,5-didehydro-PGF$_1$α-type compound of formula XXXI.

Further following the transformation of the formula XXXIII compound of Chart D to the formula XXXVI and XXXVII compounds, the formula XLIV compound of Chart C is transformed to the formula XLV and formula XLVI prostacyclin analogs: the (5S)-6β-PGI$_1$-type and (5R)-6α-PGI$_1$-type compounds described herein.

With respect to the identification of the various isomeric products herein, physical and analytical data may be employe to determine assignment of configuration at C-5 and C-6 for mixtures of products obtained by the processes of the above charts. However, an especially convenient metho for determining polarity of isomeric mixtures is by thin layer chromatographic analysis. Accordingly, each of the 6α-isomers will appear less polar than either of the corresponding 6β-isomers by silica gel TLC in most solvent systems. As between the (5S) and (5R) forms of the 6β-isomers, the more polar isomer will be the (5R) isomeric form. In contrast, for the 6α-PGI$_1$ isomers, the (5S) form will appear in most silica gel TLC solvents systems to be more polar than the corresponding (5R) form. Accordingly, with respect to the isomeric formula XXXVI and formula XXXVII products of Chart B, the more polar isomer will be the 6β-isomer of formula XXXVII, and similarly in Chart C the formula XLI 6β-PGI$_1$ isomer will be the more polar of the formula XLV and formula XLVI isomeric products.

When the compounds above are prepared as esters and acids are desired, saponification yields the corresponding carboxylic acid. For the acids thusly prepared, the corresponding pharmacologically acceptable salts thereof are prepared by neutralization with the base corresponding to the salt to be prepared.

With respect to the novel PG-type amides ($X_1$ is —COL$_3$) and p-substituted phenyl esters ($X_1$ is —COL$_5$), such compounds are prepared as follows:

With regard to the preparation of the p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PGF-type carboxylic acids, the corresponding carboxyamides are prepared by one of several amidation methods known in the prior art. See, for example, U.S. Pat. No. 3,981,868, issued Sept. 21, 1976 for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the 9-deoxy-9methylene-PGF-type acids are prepared is, first, by transformation of such free acids to corresponding mixed acid anhydrides. By this procedure, the prostaglandin-type free acid is first neutralized with an equivalent of an amine base, and thereafter reacted a slight stoichiometric excess of a chloroformate corresponding to the mixed anhydride to be prepared.

The amine base preferred for neutralization is triethylamine, although other amines (e.g. pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGF-type free acid is mixed with both the tertiary amine base and the chloroformate in a suitable solvent (e.g. aqueous tetrahydrofuran), allowing the reaction to proceed at −10° to 20° C.

Thereafter, the mixed anhydride is converted to the corresponding amido or cycloamido derivative by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about −10° to +10° C., until the reaction is shown to be complete. For highly volatile amines, acid addition salts thereof (e.g., methylamine hydrochloride) are employed in place of the corresponding free base (e.g. methylamine).

Thereafter, the novel PGF-type amido or cycloamido derivative is recovered from the reaction mixture by conventional techniques.

The carbonylamido and sulfonylamido derivatives of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl of sulfonyl isocyanate, corresponding to the carbonylamido of sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure PG-type sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 spectrophotometer on deuterochloroform solutions with tetramethylsilane as an internal standard.

Mass spectra are recorded on a CEC model 21-110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine," herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns of Thomas-Hoover melting point apparatus.

DDQ refers to 2,3-dichloro-5,6-dicyano-1,4-benzoquinone.

EXAMPLE 1

5-Hydroxy-PGI$_1$, methyl ester (Formula IV: X$_1$ is —COOCH$_3$, Z$_1$ is —(CH$_2$)$_3$—, $p$ and $q$ are 0, R$_8$ is hydroxy, Y$_1$ is trans-CH=CH—, R$_3$ and R$_4$ of the L$_1$ moiety and R$_5$ of the M$_1$ moiety are all hydrogen, and R$_7$ is n-butyl) and the corresponding free acids.

Refer to Chart A (optional procedure).

A. Mercuric acetate (10 g.) is dissolved in 70 ml. of deionized water and the resulting mixture treated with 70 ml. of tetrahydrofuran with stirring. A resulting bright yellow suspension is then treated with PGF$_2\alpha$, methyl ester (5.02 g.) in tetrahydrofuran (70 ml.), followed by rinsing with additional tetrahydrofuran (30 ml.). The resulting mixture is then stirred for an additional two hours, concentrated under reduced pressure, and extracted with ethyl acetate. The organic extracts are then washed with water, dried over magnesium sulfate, filtered and evaporated under reduced pressure to yield 11.53 g. of the formula XXII intermediate.

B. The reaction product of Part A (22.47 g.) is dissolved in methanol, yielding a total volume of 150 ml. of solution. Thereafter, the methanolic solution is treated with 125 ml. of saturated aqueous sodium chloride and stirred at ambient temperature for 2 hours. Concentrating the solution to about ½ its original volume, extracting with ethyl acetate, washing the ethyl acetate extracts with brine, drying over magnesium sulfate, and concentrating to dryness yields 18.87 g. of crude formula XXIII intermediate. Chromatographing on 1.5 kg. of silica gel with 75% ethyl acetate in Skellysolve B as the eluant yields pure formula XXIII intermediate in two forms: the less polar 6α-PGI$_1$-type formula XXIII intermediates (5.11 g.) and the more polar 6β-PGI$_1$-type formula XXIII intermediates (9.67 g.).

C. Sodium borohydride (145 mg.) and dimethylformamide (15 ml.) are placed in a flask which can be supplied with oxygen, the flow of which is adjusted so as to create a vigorously bubbling solution. After saturation of the solution with oxygen (about 15 minutes), the formula XXIII 6β-PGI$_1$-type intermediate (1.645 g.) dissolved in dimethylformamide (25 ml.) and likewise saturated with oxygen is added to the borohydride solution dropwise over about 30 minutes. After an additional 20 min., the resulting solution is then centrifuged to separate mercury and poured into a 5% aqueous potassium bisulfite solution and extracted with diethyl ether. The ethereal extracts are then combined, washed with water and brine, dried over magnesium sulfate, filtered, and concentrated under reduced pressure to yield 0.786 g. of formula XXV product. Extracting the aqueous layer with ethyl acetate yields another 0.167 g. of formula XXV product for a total of 0.953 g. of epimerically mixed formula XXV 6β-PGI$_1$-type products: (5RS)-5-hydroxy-6β-PGI$_1$, methyl ester.

(5RS)-5-hydroxy-6β-PGI$_1$, methyl ester (1.394 g.) is then chromatographed on silica gel (HPLC), eluting with 40% ethyl acetate in hexane. Accordingly there is obtained 0.570 g. of the less polar isomer, (5S)-5-hydroxy-6β-PGI$_1$, methyl ester, which yields 458 mg. of a pure white solid, m.p. 97.5°-99°, on recrystallization from ethyl acetate and hexane. Likewise, there is obtained the more polar product, (5R)-5-hydroxy-6β-PGI$_1$, methyl ester (0.54 g.), yielding 318 mg. of a white solid, m.p. 94°-95°, on recrystallization from acetone and hexane.

For the (5S) isomer, the mass spectrum of the trimethylsilyl derivative exhibits a high resolution peak at 600.3711 and other peaks at 585, 569, 529, 510, 415.2156 (a high resolution peak), 397, 307, 203, 173, and 171. For the (5R) isomer, a high resolution peak is observed at 600.3717 and other peaks as for the (5S) isomer.

Infrared absorptions for the (5S) isomer are observed at 3540, 3440, 1735, 1715, 1345, 1310, 1245, 1205, 1175, 1070, 1045, 1025 and 975 cm$^{-1}$. The C:H ratio is 65.92:9.48.

For the (5R) isomer, infrared absorptions are observed at 3440, 1735, 1715, 1320, 1250, 1205, 1185, 1080, 1070, 1050, 1025, and 970 cm$^{-1}$. The C:H ratio is 65.86:9.58.

D. Following the procedure of Part C above, but employing 2.71 g. of the formula XXIII 6α-PGI$_1$-type intermediate, there are obtained 450 mg. of the less polar 6α-PGI$_1$-type product, (5R)-5-hydroxy-6α-PGI$_1$, methyl ester; and 180 mg. of the more polar 6α-PGI$_1$-type product, (5S)-5-hydroxy-6α-PGI$_1$, methyl ester.

E. A solution of (5R)-5-hydroxy-6β-PGI$_1$, methyl ester (225 mg.) in methanol (8 ml.) is treated with 12 ml. of 0.1 N aqueous sodium hydroxide and stirred at ambient temperature. The methanol is then removed under reduced pressure and the aqueous residue acidified with 10% potassium bisulfate in ethyl acetate. The layers are separated and the aqueous layer extracted with ethyl acetate. The combined organic extracts are washed with water and brine, dried over magnesium sulfate, and concentrated under reduced pressure to yield a white solid (218 mg.) of crude free acid. The solid is then crystallized from ethyl acetate in hexane, yielding 168 mg. of pure title product. Melting point is 102°–104° C. The C:H ratio is 64.67:9.42. The high resolution mass spectrum for the trimethylsilyl derivative exhibits a peak at 658.3934 and other peaks are observed at 643, 587, 568, 553, 497, 425, 397, 307, 261, 173, and 171.

Following the saponification procedure described above, 387 mg. of the (5S)-5-hydroxy-6β-PGI$_1$, methyl ester of Part C is transformed to 354 mg. of corresponding free acid, which on recrystallization from acetone and hexane yields a substance whose melting point is 133°–137° C. The C:H ratio is 64.90:9.36. The high resolution mass spectrum for the trimethylsilyl derivative exhibits a peak at 658.3914 with other peaks as described for (5R)-5-hydroxy-6β-PGI$_1$, above.

Further following the procedure for the preparation of (5R)-5-hydroxy-6β-PGI$_1$, there are obtained 304 mg. of (5R)-5-hydroxy-6α-PGI$_1$, from 330 mg. of the corresponding methyl ester and 110 mg. of (5S)-5-hydroxy-6α-PGI$_1$, from 138 mg. of the corresponding methyl ester.

Further following the procedure of Example 1, there are obtained each of the various methyl esters and corresponding free acids of formula XXV 5-hydroxy-PGI$_1$-type compounds from each of the various corresponding PGF-type compounds of formula XXI.

EXAMPLE 2

(5S)-5-Hydroxy-6α-PGI$_1$, methyl ester and (5R)-5-hydroxy-6β-PGI$_1$, methyl ester Refer to Chart B.

A. To a stirred solution of PGF$_1$α, methyl ester (25.89 g.) in 110 ml. of dimethylformamide is added t-butyldimethylsilyl chloride (52.98 g.) and imidazole (47.88 g.). The resulting solution is stirred at ambient temperature for 12 hours and thereafter the reaction mixture is cooled in an ice water bath and quenched with 15–20 g. of crushed ice. The resulting mixture is then diluted with 200 ml. of water and extracted with diethyl ether. The combined ethereal extracts are then successively washed with water, saturated with aqueous ammonium chloride, water and brine; dried over anhydrous sodium sulfate; and concentrated under reduced pressure yielding 49.88 g. of the formula XXXII tris-(t-butyldimethylsilyl ether) of PGF$_2$α, methyl ester as a viscous yellow oil. NMR absorptions are observed at 5.40, 4.30–3.70, 3.62, 2.5–1.1, 0.91, 0.88, 0.08 and 0.02 δ.

B. m-Chloroperbenzoic acid (4.22 g.) is added in one portion to a stirred suspension of the reaction product of Part A (14.58 g.) and sodium bicarbonate (1.73 g.) in 400 ml. of chloroform and ice water bath. The resulting mixture is then stirred at ice bath temperature for about 7 hours and thereafter the layers are separated and the chloroform layer washed successively with 5% aqueous sodium bicarbonate, 10% aqueous sodium sulfite, 5% aqueous sodium bicarbonate, water, and brine. Thereafter the chloroform layer was dried over anhydrous sodium sulfate and concentrated under reduced pressure to yield 14.95 g. of crude formula XXXIII cis epoxides, i.e., (5S,6R)-isomer and (5R,6S)-isomer, hereinafter respectively "beta" and "alpha" isomers.

This crude product is then chromatographed on 750 g. of silica gel packed with Skellysolve B and ethyl acetate (20:1) and eluted with the same mixture of ethyl acetate and Skellysolve B. The resulting 10.04 g. of mixed formula XXXIII product is then subjected to high pressure liquid chromatography, eluting with Skellysolve B and ethyl acetate (35:1), yielding 3.82 g. of a 1:1 mixture of formula XXXIII epoxides, 0.350 g. of greater than 80% pure α-epoxide, and 3.12 g. of an uncharacterized mixture of epoxides. Silica gel TLC Rf in Skellysolve B and ethyl acetate (15:1) is 0.50 (α-epoxide) and 0.48 (β-epoxide). NMR absorptions are observed at 5.50, 4.45–3.70, 3.67, 3.10–1.10, 0.98, 0.96, 0.95, 1.10, 0.09 and 0.04 δ. Infrared absorptions are observed at 2900, 1740, 1460, 1250, 1060, 885, and 770 cm$^{-1}$. The C:H ratio is 64.79:11.81. The mass spectrum exhibits a weak molecular ion at 726, and a high resolution peak at 669.4398.

C. n-Butylammonium fluoride (a 1.2 molar solution in tetrahydrofuran; 20 ml.) is added to a stirred solution of the reaction product of Part B (3.45 g.) in 30 ml. of tetrahydrofuran under a nitrogen atmosphere. The reaction mixture is maintained at ambient temperature for 21 hours, at which time the resulting mixture is then diluted with saturated brine and extracted with ethyl acetate. The combined organic extracts are then washed with brine, dried over sodium sulfate, and concentrated under reduced pressure to yield 9.465 g. of a viscous brown oil. This oil is then chromatographed on 270 g. of silica gel packed with dichloromethane in acetone (2:1) and eluted with 67–33% dichloromethane in acetone, yielding 1.247 g. of a mixture of formula XXXIV desilylated epoxide and formula XXXV epimerically mixed title product.

NMR absorptions are observed at 5.70–5.15, 4.31–3.50, 3.00–1.00 and 0.90 δ. Characteristic infrared absorptions are observed at 3400, 2925, 1760, 1440, 1210, 1160, and 970 cm$^{-1}$. The high resolution mass spectrum for the trimethylsilyl derivative exhibits a peak at 496.3027.

D. The mixture of formula XXXIV and formula XXXV compounds of Part C (1.147 g.) in 180 ml. of dichloromethane and 45 g. of acid-washed silica gel is stirred at ambient temperature for 20 hours. Thereafter the silica gel is removed by filtration through diatomaceous earth and the filter cake washed with acetone. Concentration under reduced pressure yields a mixture of isomeric title products which is chromatographed by high pressure liquid chromatography, eluting with acetone and hexane (1:1) and yielding 0.069 g. of (5S)-5-hydroxy-6α-PGI$_1$, methyl ester, 0.10 g. of the epimeric mixture and 0.130 g. of pure (5R)-5-hydroxy-6β-PGI$_2$, methyl ester. Recrystallization of the 6β-isomer from hexane and acetone yields product with a melting point of 94°–96° C.

For the (5R)-5-hydroxy-6β-PGI$_1$, methyl ester, NMR absorptions are observed at 5.50, 4.40, 4.30–2.70, 3.67, and 2.50–1.00 δ. For the 6α-isomer, NMR absorptions are observed at 5.50, 4.40–3.10, 3.67, 2.60, 1.10 and 0.90 δ. For both isomers, the high resolution mass spectrum of the trimethylsilyl derivative exhibits a peak at 600.3687.

Following the procedure of Example 2, there are prepared from the various formula XXXI PGF-type reactants the formula XXXVI (5R)-6β-PGI$_1$-type compounds and the formula XXXVII (5R)-5-hydroxy-6α-PGI$_1$-type products.

EXAMPLE 3

(5S)-5-hydroxy-6β-PGI$_1$, methyl ester and
(5R)-5-hydroxy-6α-PGI$_1$, methyl ester Refer to Chart C.

A. The reaction product of Part A of Example 2 (5 g.) in 125 ml. of acetone and 18 ml. of water is cooled in an ice water bath and 1.007 g. of N-methyl-morpholine-N-oxide dihydrate and 80 mg. of osmium tetraoxide (20 mg./ml. in a solution of tert-butanol, 4 ml.). The resulting mixture is then stirred at ambient temperature for 16 hours and thereafter the acetone removed under reduced pressure. The residual oil is then diluted with crushed ice water and acidified to about pH 5 with 2N potassium sulfate. The aqueous layer is then extracted with 450 ml. of diethyl ether and the ethereal extracts are washed with water and brine, dried over sodium sulfate, and concentrated under reduced pressure to yield 4.65 g. of crude formula XLII glycol. 4.124 g. of the glycol is then chromatographed on 220 g. of silica gel packed with Skellysolve B and ethyl acetate (4:1) and eluted with the same mixture of Skellysolve B and ethyl acetate, yielding 3.317 g. of the epimerically mixed glycol, (5R,6S) and (5S,6R) formula XLII glycols. Silica gel TLC Rf is 0.34 and 0.29 in Skellysolve B and ethyl acetate (3:1). NMR absorptions are observed at 5.45, 4.35, 3.10, 3.63, 2.90–1.10, 0.91, 0.87, 0.08, 0.03, and 0.02 δ.

B. p-Toluenesulfonyl chloride (0.850 g.) is added to a stirred solution of the reaction product of Part A (3.317 g.) in 30 ml. of pyridine, cooled in an ice-water bath. Progress of the reaction is monitored by silica gel TLC and at the end of about 20 hours, the reaction mixture is combined with an additional 4.30 g. of p-toluenesulfonyl chloride and the reaction continued at ambient temperature for an additional 17 hours. Thereupon the reaction mixture is quenched by addition of 5–10 g. of crushed ice and the resulting mixture stirred for 10–15 min., diluted with 115 ml. of water, and the aqueous layer extracted with diethyl ether. The ethereal extracts are then washed successively with 5% aqueous sodium bicarbonate, ice cold 5% aqueous hydrochloric acid, water, and saturated brine; dried over sodium sulfate; and concentrated under reduced pressure to yield 3.612 g. of crude formula XLIIIa and formula XLIIIb mono p-toluenesulfonates. These mixed monyl sulfonates are then chromatographed on 220 g. of silica gel, packed and eluted with Skellysolve B in ethyl acetate (5:1), yielding 2.590 g. of pure formula XLIIIa and XLIIIb products as a viscous yellow oil. NMR absorptions are observed at 7.82, 7.35, 5.45, 4.80–3.50, 3.63, 2.50, 2.50–1.10, 0.97, 0.13, and 0.03 δ.

C. To a stirred suspension of sodium hydride (0.160 g.) as a 50% oil dispersion) and 10 ml. of dimethylformamide cooled to 0° C. is added the reaction product of Part B in 20 ml. of dimethylformamide over a period of 6 minutes. The resulting mixture is then stirred at ambient temperature for 3 hours and thereafter the reaction mixture is cooled in an ice water bath to about 0° C. The reaction is then quenched by addition of 5 g. of crushed ice and the resulting mixture diluted with 50 ml. of water and extracted with diethyl ether. The ethereal extracts are then washed with water and brine, dried over sodium sulfate, and concentrated under reduced pressure to yield 1.745 g. of the epimeric mixture of formula XLIV trans epoxides, the (5S,6S) and (5R,6R) epoxides.

This crude product is then chromatographed on 65 g. of silica gel packed and eluted with Skellysolve B and ethyl acetate (15:1), yielding 1.446 g. of the pure formula XLIV mixed epoxides. Silica gel TLC Rf is 0.49 and 0.53 in Skellysolve B and ethyl acetate (15:1). NMR absorptions are observed at 5.47, 4.35–3.70, 3.67, 2.70–1.10, 0.97, 0.91, 0.10, and 0.03 δ. Infrared absorptions are observed at 2990, 1740, 1460, 1250, 1060, 835, and 770 cm$^{-1}$. The high resolution mass spectrum for the trimethylsilyl derivative exhibits a peak at 669.4392 and a weak molecular ion is observed at 726.

D. Following the procedure of Example 2, Part C and D, the reaction product of Part C above (1.263 g.) is transformed to 91 mg. of pure (5R)-5-hydroxy-6α-PGI$_1$, methyl ester, 96 mg. of a mixture of formula XLV and formula XLVI 5-hydroxy-PGI$_1$ methyl esters and 72 mg. of pure (5R)-5-hydroxy-6β-PGI$_1$, methyl ester. Recrystallization of the latter compound yields fluffy white crystals (melting point 98°–99° C).

For the (5S)-5-hydroxy-6β-PGI$_1$, methyl ester, NMR absorptions are observed at 5.50, 4.42, 4.25–2.95, 3.67, 2.80–1.10, and 0.90 δ. The high resolution mass spectrum for the trimethylsilyl derivative exhibits a peak at 600.3662.

For the (5R)-5-hydroxy-6β-PGI$_1$, methyl ester, NMR absorptions are observed at 5.50, 4.40–2.75, 3.67, 2.70–1.10, and 0.90 δ. The high resolution mass spectrum for the trimethylsilyl derivative exhibits a peak at 600.3687.

Following the procedure of Example 3, but employing each of the various formula XLI compounds of Chart C, there are prepared the various formula XLV (5S)-5-hydroxy-6β-PGI$_1$-type and formula XLVI (5R)-5-hydroxy-6β-PGI$_1$-type compounds of the present invention.

Following the procedure of the above examples, but employing the appropriate PGF$_2$β-type, cis-4,5-didehydro-PGF$_2$β-type, 9-deoxy-9-hydroxymethyl-PGF$_2$-type, or 9-deoxy-9-hydroxymethyl-cis-4,5-didehydro-PGF$_1$-type starting material, there are prepared
(5S)-5-hydroxy-6α-PGI$_1$-type compounds;
(5R)-5-hydroxy-6α-PGI$_1$-type compounds;
(5S)-5-hydroxy-6β-PGI$_1$-type compounds; or (5R)-5-hydroxy-6β-PGI$_1$-type compounds in free acid, amide, or ester from which exhibit the following side chain substituents:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-; 16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tretranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-Phenoxy-18,19,20-trinor-13-cis-;
16-Methyl-16-phenoxy-18,19,20-trinor-13-cis-;
2,2-Difluoro-;
2,2-Difluoro-15-methyl-;
2,2-Difluoro-16-methyl-;
2,2-Difluoro-16,16-dimethyl-;
2,2-Difluoro-16-fluoro-;

2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,19,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-phenyl-18,19,20-trinor-13,14-didehydro-;
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)17,18,19,20-tetranor-13,14-dihydro-;
2,2-Difluoro-16-phenyl-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
2,2-Difluoro-13-cis-;
2,2-Difluoro-16-methyl-13-cis-;
2,2-Difluoro-16,16-dimethyl-13-cis-;
2,2,16-Trifluoro-13-cis-;
2,2,16,16-Tetrafluoro-13-cis-;
2,2-Difluoro-17-phenyl-18,19,20-trinor-13-cis-;
2,2-Difluoro-17-(m-trifluoromethylphenyl)-18,19,20-trinor-13-cis-;
2,2-Difluoro-17-(m-chlorophenyl)-18,19,20-trinor-13-cis-;
2,2-Difluoro-17-(p-fluorophenyl)-18,19,20-trinor-13-cis-;
2,2-Difluoro-16-methyl-17-phenyl-18,19,20-trinor-13-cis-;
2,2-Difluoro-16,16-dimethyl-17-phenyl-18,19,20-trinor-13-cis-;
2,2,16-Trifluoro-17-phenyl-18,19,20-trinor-13-cis-;
2,2-Difluoro-16-phenyl-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;

2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
2,2-Difluoro-13-cis-;
2,2-Difluoro-16-methyl-13-cis-;
2,2-Difluoro-16,16-dimethyl-13-cis-;
2,2,16-Trifluoro-13-cis-;
2,2,16,16-Tetrafluoro-13-cis-;
2,2-Difluoro-17-phenyl-18,19,20-trinor-13-cis-;
2,2-Difluoro-17-(m-trifluoromethylphenyl)-18,19,20-trinor-13-cis-;
2,2-Difluoro-17-(m-chlorophenyl)-18,19,20-trinor-13-cis-;
2,2-Difluoro-17-(p-fluorophenyl)-18,19,20-trinor-13-cis-;
2,2-Difluoro-16-methyl-17-phenyl-18,19,20-trinor-13-cis-;
2,2-Difluoro-16,16-dimethyl-17-phenyl-18,19,20-trinor-13-cis-;
2,2,16-Trifluoro-17-phenyl-18,19,20-trinor-13-cis-;
2,2,16,16-Tetrafluoro-17-phenyl-18,19,20-trinor-13-cis-;
2,2-Difluoro-16-phenyl-17,18,19,20-tetranor-13-cis-;
2,2-Difluoro-16-(m-trifluoromethylphenyl)-17,18,19,20-tetranor-13-cis-;
2,2-Difluoro-16-(m-chlorophenyl)-17,18,19,20-tetranor-13-cis-;
2,2-Difluoro-16-(p-fluorophenyl)-17,18,19,20-tetranor-13-cis-;
2,2-Difluoro-16-phenyl-18,19,20-trinor-13-cis-;
2,2-Difluoro-16-methyl-16-phenyl-18,19,20-trinor-13-cis-;
2,2-Difluoro-16-phenoxy-17,18,19,20-tetranor-13-cis-;
2,2-Difluoro-16-(m-trifluoromethylphenoxy)-17,18,19,20-tetranor-13-cis-;
2,2-Difluoro-16-(m-chlorophenoxy)-17,18,19,20-tetranor-13-cis-;
2,2-Difluoro-16-(p-fluorophenoxy)-17,18,19,20-tetranor-13-cis-;
2,2-Difluoro-16-phenoxy-18,19,20-trinor-13-cis-;
2,2-Difluoro-16-methyl-16-phenoxy-18,19,20-trinor-13-cis-;
trans-2,3-Didehydro-;
trans-2,3-Didehydro-15-methyl-;
trans-2,3-Didehydro-16-methyl-;
trans-2,3-Didehydro-16,16-dimethyl-;
trans-2,3-Didehydro-16-fluoro-;
trans-2,3-Didehydro-16,16-difluoro-;
trans-2,3-Didehydro-17-phenyl-18,19,20-trinor-;
trans-2,3-Didehydro-17-(m-trifluoromethylphenyl)-18,19,20-trinor-;
trans-2,3-Didehydro-17-(m-chlorophenyl)-18,19,20-trinor-;
trans-2,3-Didehydro-17-(p-fluorophenyl)-18,19,20-trinor-;
trans-2,3-Didehydro-16-methyl-17-phenyl-18,19,20-trinor-;
trans-2,3-Didehydro-16,16-dimethyl-17-phenyl-18,19,20-trinor-;
trans-2,3-Didehydro-16-fluoro-17-phenyl-18,19,20-trinor-;
trans-2,3-Didehydro-16,16-difluoro-17-phenyl-18,19,20-trinor-;
trans-2,3-Didehydro-16-phenyl-17,18,19,20-tetranor-;
trans-2,3Didehydro-16-(m-trifluoromethylphenyl)-17,18,19,20-tetranor-;
trans-2,3-Didehydro-16-(m-chlorophenyl)-17,18,19,20-tetranor-;
trans-2,3-Didehydro-16-(p-fluorophenyl)-17,18,19,20-tetranor-;
trans-2,3-Didehydro-16-phenyl-18,19,20-trinor-;
trans-2,3-Didehydro-16-methyl-16-phenyl-18,19,20-trinor-;
trans-2,3-Didehydro-16-phenoxy-17,18,19,20-tetranor-;
trans-2,3-Didehydro-16-(m-trifluoromethylphenoxy)-17,18,19,20-tetranor-;
trans-2,3-Didehydro-16-(m-chlorophenoxy)-17,18,19,20-tetranor-;
trans-2,3-Didehydro-16-(p-fluorophenoxy)-17,18,19,20-tetranor-;
trans-2,3-Didehydro-16-phenoxy-18,19,20-trinor-;
trans-2,3-Didehydro-17-(m-chlorophenyl)-18,19,20-trinor-;
trans-2,3-Didehydro-17-(p-fluorophenyl)-18,19,20-trinor-;
trans-2,3-Didehydro-16-methyl-17-phenyl-18,19,20-trinor-;
trans-2,3-Didehydro-16,16-dimethyl-17-phenyl-18,19,20-trinor-;
trans-2,3-Didehydro-16-fluoro-17-phenyl-18,19,20-trinor-;
trans-2,3-Didehydro-16,16-difluoro-17-phenyl-18,19,20-trinor-;
trans-2,3-Didehydro-16-phenyl-17,18,19,20-tetranor-;
trans-2,3-Didehydro-16-(m-trifluoromethylphenyl)-17,18,19,20-tetranor-;
trans-2,3-Didehydro-16-(m-chlorophenyl)-17,18,19,20-tetranor-;
trans-2,3-Didehydro-16-(p-fluorophenyl)-17,18,19,20-tetranor-;
trans-2,3-Didehydro-16-phenyl-18,19,20-trinor-;
trans-2,3-Didehydro-16-methyl-16-phenyl-18,19,20-trinor-;
trans-2,3-Didehydro-16-phenoxy-17,18,19,20-tetranor-;
trans-2,3-Didehydro-16-(m-trifluoromethylphenoxy)-17,18,19,20-tetranor-;
trans-2,3-Didehydro-16-(m-chlorophenoxy)-17,18,19,20-tetranor-;
trans-2,3-Didehydro-16-(p-fluorophenoxy)-17,18,19,20-tetranor-;
trans-2,3-didehydro-16-phenoxy-18,19,20-trinor-;
trans-2,3-Didehydro-16-methyl-16-phenoxy-18,19,20-trinor-;
trans-2,3-Didehydro-13,14-didehydro-;
trans-2,3-Didehydro-16-methyl-13,14-didehydro-;
trans-2,3-Didehydro-16,16-dimethyl-13,14-didehydro-;
trans-2,3-Didehydro-16-fluoro-13,14-didehydro-;
trans-2,3-Didehydro-16,16-difluoro-13,14-didehydro-;
trans-2,3-Didehydro-17-phenyl-18,19,20-trinor-13,14-didehydro-;
trans-2,3-Didehydro-17-(m-trifluoromethylphenyl)-18,19,20-trinor-13,14-didehydro-;
trans-2,3-Didehydro-17-(m-chlorophenyl)-18,19,20-trinor-13,14-didehydro-;
trans-2,3-Didehydro-17-(p-fluorophenyl)-18,19,20-trinor-13,14-didehydro-;
trans-2,3-Didehydro-16-methyl-17-phenyl-18,19,20-trinor-13,14-didehydro-;
trans-2,3-Didehydro-16,16-dimethyl-17-phenyl-18,19,20-trinor-13,14-didehydro-;
trans-2,3-Didehydro-16-fluoro-17-phenyl-18,19,20-trinor-13,14-didehydro-;

trans-2,3-Didehydro-16,16-difluoro-17-phenyl-18,19,20-trinor-13,14-didehydro;
trans-2,3-Didehydro-16-phenyl-17,18,19,20-tetranor-13,14-didehydro-;
trans-2,3-Didehydro-16-(m-trifluoromethylphenyl)-17,18,19,20-tetranor-13,14-didehydro:;
trans-2,3-Didehydro-16-(m-chlorophenyl)-17,18,19,20-tetranor-13,14-didehydro-;
trans-2,3-Didehydro-16-phenyl-18,19,20-trinor-13,14-didehydro-;
trans-2,3-Didehydro-16-methyl-16-phenyl-18,19,20-trinor-13,14-didehydro-;
trans-2,3-Didehydro-16-phenoxy-17,18,19,20-tetranor-13,14-didehydro-;
trans-2,3-Didehydro-16-(m-trifluoromethylphenyl)-17,18,19,20-tetranor-13,14-didehydro-;
trans-2,3-Didehydro-16-(m-chlorophenoxy)-17,18,19,20-tetranor-13,14-didehydro-;
trans-2,3-Didehydro-16-phenoxy-18,19,20-trinor-13,14-didehydro-;
trans-2,3-Didehydro-16-methyl-16-phenoxy-18,19,20-trinor-13,14-didehydro-;
trans-2,3-Didehydro-13,14-dihydro-;
trans-2,3-Didehydro-16-methyl-13,14-dihydro-;
trans-2,3-Didehydro-16,16-dimethyl-13,14-dihydro:;
trans-2,3-Didehydro-16-fluoro-13,14-dihydro-;
trans-2,3-Didehydro-16,16-difluoro-13,14-dihydro-;
trans-2,3-Didehydro-17-phenyl-18,19,20-trinor -13,14-dihydro-;
trans-2,3-Didehydro-17-(m-trifluoromethylphenyl)-18,19,20-trinor-13,14-dihydro-;
trans-2,3-Didehydro-17-(m-chlorophenyl)18,19,20-trinor-13,14-dihydro-;
trans-2,3-Didehydro-17-(p-fluorophenyl)-18,19,20-trinor-13,14-dihydro-;
trans-2,3-Didehydro-16-methyl-17-phenyl-18,19,20-trinor-13,14-dihydro-;
trans-2,3-Didehydro-16,16-dimethyl-17-phenyl-18,19,20-trinor-13,14-dihydro-;
trans-2,3-Didehydro-16-fluoro-17-phenyl-18,19,20-trinor-13,14-dihydro-;
trans-2,3-Didehydro-16,16-difluoro-17-phenyl-18,19,20-trinor-13,14-dihydro-;
trans-2,3-Didehydro-16-phenyl-17,18,19,20-tetranor-13,14-dihydro-;
trans-2,3-Didehydro16-(m-trifluoromethylphenyl)-17,18,19,20-tetranor-13,14-dihydro-;
trans-2,3-Didehydro-16-(m-chlorophenyl)-17,18,19,20-tetranor-13,14-dihydro-;
trans-2,3-Didehydro-16-(p-fluorophenyl)-17,18,19,20-tetranor-13,14-dihydro-;
trans-2,3-Didehydro-16-phenyl-18,19,20-trinor-13,14-dihydro-;
trans-2,3-Didehydro-16-methyl-16-phenyl-18,19,20-trinor-13,14-dihydro-;
trans-2,3-Didehydro-16-phenoxy-17,18,19,20-tetranor-13,14-dihydro-;
trans-2,3-Didehydro-16-(m-trifluoromethylphenoxy)-17,18,19,20-tetranor-13,14-dihydro-;
trans-2,3-Didehydro-16-(m-chlorophenoxy)-17,18,19,20- tetranor-13,14-dihydro-;
trans-2,3-Didehydro-16-(p-fluorophenoxy)-17,18,19,20-tetranor-13,14-dihydro-;
trans-2,3-Didehydro-16-phenoxy-18,19,20-trinor-13,14-dihydro-;
trans-2,3-Didehydro-16-methyl-16-phenoxy-18,19,20-trinor-13,14-dihydro-;
trans-2,3-Didehydro-13-cis-;
trans-2,3-Didehydro-16-methyl-13-cis-;
trans-2,3-Didehydro-16-fluoro-17-phenyl-18,19,20-trinor-13,14-dihydro-;
trans-2,3-Didehydro-16,16-difluoro-17-phenyl-18,19,20-trinor-13,14-dihydro-;
trans-2,3-Didehydro-16-phenyl-17,18,19,20-tetranor-13,14-dihydro-;
trans-2,3-Didehydro-16-(m-trifluoromethylphenyl)-17,18,19,20-tetranor-13,14-dihydro-;
trans-2,3-Didehydro-16-(m-chlorophenyl)-17,18,19,20-tetranor-13,14-dihydro-;
trans-2,3-Didehydro-16-(p-fluorophenyl)-17,18,19,20-tetranor-13,14-dihydro-;
trans-2,3-Didehydro-16-phenyl-18,19,20-trinor-13,14-dihydro-;
trans-2,3-Didehydro-16-methyl-16-phenyl-18,19,20-trinor-13,14-dihydro-;
trans-2,3-Didehydro-16-phenoxy-17,18,19,20-tetranor-13,14-dihydro-;
trans-2,3-Didehydro-16-(m-trifluoromethylphenoxy)-17,18,19,20-tetranor-13,14-dihydro-;
trans-2,3-Didehydro-16-(m-chlorophenoxy)-17,18,19,20-tetranor-13,14-dihydro-;
trans-2,3-Didehydro-16-(p-fluorophenoxy)-17,18,19,20-tetranor-13,14-dihydro-;
trans-2,3-Didehydro-16-phenoxy-18,19,20-trinor-13,14-dihydro-;
trans-2,3-Didehydro-16-methyl-16-phenoxy-18,19,20-trinor-13,14-dihydro-;
trans-2,3-Didehydro-13-cis-;
trans-2,3-Didehydro-16-methyl-13-cis-;
trans-2,3-Didehydro-16,16-dimethyl-13-cis-;
trans-2,3-Didehydro-16-difluoro-13-cis-;
trans-2,3-Didehydro-16,16-difluoro-13-cis-;
trans-2,3-Didehydro-17-phenyl-18,19,20-trinor-13-cis-;
trans-2,3-Didehydro-17-(m-trifluoromethylphenyl)-18,19,20-trinor-13-cis-;
trans-2,3-Didehydro-17-(m-chlorophenyl)-18,19,20-trinor-13-cis-;
trans-2,3-Didehydro-17-(p-fluorophenyl)-18,19,20-trinor-13-cis-;
trans-2,3-Didehydro-16-methyl-17-phenyl-18,19,20-trinor-13-cis-;
trans-2,3-Didehydro-16,16-dimethyl-17-phenyl-18,19,20-trinor-13-cis-;
trans-2,3-Didehydro-16-fluoro-17-phenyl-18,19,20-trinor-13-cis-;
trans-2,3-Didehydro-16,16-difluoro-17-phenyl-18,19,20-trinor-13-cis-;
trans-2,3-Didehydro-16-phenyl-17,18,19,20-tetranor-13-cis-;
trans-2,3-Didehydro-16-(m-trifluoromethylphenyl)-17,18,19,20-tetranor-13-cis-;
trans-2,3-Didehydro-16-(m-chlorophenyl)-17,18,19,20-tetranor-13-cis-;
trans-2,3-Didehydro-16-(p-fluorophenyl)-17,18,19,20-tetranor-13-cis-;
trans-2,3-Didehydro-16-phenyl-18,19,20-trinor-13-cis-;
trans-2,3-Didehydro-16-methyl-16-phenyl-18,19,20-trinor-13-cis-;
trans-2,3-Didehydro-16-phenoxy-17,18,19,20-tetranor-13-cis-;
trans-2,3-Didehydro-16-(m-trifluoromethylphenoxy)-17,18,19,20-tetranor-13-cis-;
trans-2,3-Didehydro-16-(m-chlorophenoxy)-17,18,19,20-tetranor-13-cis-;
trans-2,3-Didehydro-16-(p-fluorophenoxy)-17,18,19,20-tetranor-13-cis-;

trans-2,3-Didehydro-16-phenoxy-18,19,20-trinor-13-cis-;

trans-2,3-Didehydro-16-methyl-16-phenoxy-18,19,20-trinor-13-cis-;

and their corresponding 11-deoxy-PGF$_1$ and 11-deoxy-11-hydroxymethyl-PGF$_1$ analogs.

Further, following procedures described above there are prepared the corresponding 2-decarboxy-2-hydroxymethyl-PGL$_1$ and 2-decarboxy-2-aminomethyl-PGL$_1$ compounds corresponding to each of the above compounds by employing the appropriate primary alcohol or amine starting material.

Finally, the 1,5- or 1,15-lactones thereof are prepared by the method of U.S. Pat. No. 4,032,543.

We claim:

1. A prostacyclin analog of the formula

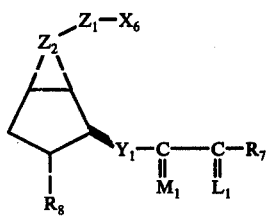

wherein R$_7$ is (1) —(CH$_2$)$_m$—CH$_3$,

(2) —(CH$_2$)$_h$—phenyl(T)$_s$, or

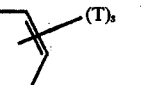

(3) —O—phenyl(T)$_s$ wherein m is 3; h is the integer zero or one; s is the integer zero, one, 2, or 3, and T is chloro, fluoro, trifluoromethyl, alkyl of one to 3 carbon atoms, inclusive, or with the proviso that not more than two T's are other than alkyl;

wherein Z$_2$ is

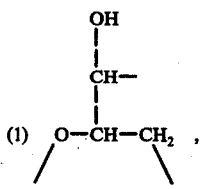 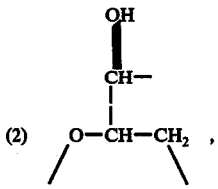

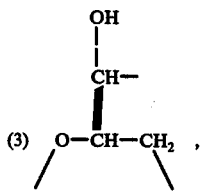 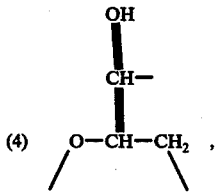

wherein Z$_1$ is (1) —(CH$_2$)$_g$—CH$_2$—CH$_2$—, (2) —(CH$_2$)$_g$—CH$_2$—CF$_2$—, or (3) trans—(CH$_2$)$_g$—CH=CH—, wherein g is the integer one, 2, or 3;

wherein R$_8$ is hydrogen, hydroxy, or hydroxymethyl;

wherein Y$_1$ is (1) trans—CH=CH—, (2) cis—CH=CH—, (3) —CH$_2$CH$_2$—, (4) trans-CH=C(Hal)—, or (5) —C≡C— wherein Hal is chloro or bromo;

wherein M$_1$ is

wherein R$_5$ is hydrogen or alkyl with one to 4 carbon atoms, inclusive;

wherein L$_1$ is

or a mixture of

wherein R$_3$ and R$_4$ are hydrogen, methyl, or fluoro, being the same or different, with the proviso that one of R$_3$ and R$_4$ is fluoro only when the other is hydrogen or fluoro;

wherein X$_6$ is (1) —COOR$_1$; wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, (2) —CH$_2$OH, (3) —CH$_2$NL$_2$L$_3$, wherein L$_2$ and L$_3$ are hydrogen, alkyl of one to 4 carbon atoms, inclusive, or —COOR$_1$, wherein R$_1$ is as defined above;

(4) —COL$_4$, wherein L$_4$ is (a) amido of the formula —NR$_{21}$R$_{22}$, wherein R$_{21}$ and R$_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive;

(b) carbonylamido of the formula —NR$_{23}$COR$_{21}$, wherein R$_{23}$ is hydrogen or alkyl of one to 4 carbon atoms and R$_{21}$ is as defined above; or (c) sulphonylamide of the formula —NR$_{23}$SO$_2$R$_{21}$, wherein R$_{21}$ and R$_{23}$ are as defined above; or (5) —COOL$_5$, wherein L$_5$ is p-substituted phenyl selected from the group consisting of

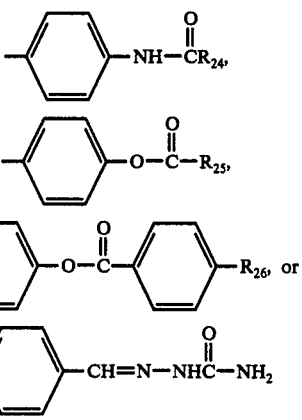

wherein R$_{24}$ is methyl, phenyl, acetamidophenyl, benzamidophenyl, or —NH$_2$; R$_{25}$ is methyl, phenyl, —NH$_2$, or methoxy; and R$_{26}$ is hydrogen or acetamido, and the 1,5— and 1,1 5-lactones thereof.

2. A prostacyclin analog according to claim 1, wherein R$_8$ is hydroxymethyl.

3. (5S)-11-Deoxy-11α-hydroxymethyl-5-hydroxy-6α-PGI$_1$, a prostacyclin analog according to claim 2.

4. A prostacyclin analog according to claim 1, wherein R$_8$ is hydrogen.

5. (5S)-11-Deoxy-5-hydroxy-6α-PGI$_1$, a prostacyclin analog according to claim 4.

6. A prostacyclin analog according to claim 1, wherein R$_8$ is hydroxy.

7. A prostacyclin analog according to claim 6, wherein Z$_2$ is

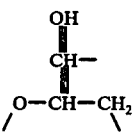

8. A prostacyclin analog according to claim 7, wherein Z$_2$ is

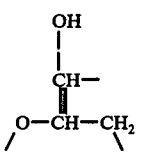

9. (5R)-5-Hydroxy-6β-PGI$_1$, a prostacyclin analog according to claim 8.

10. A prostacyclin analog according to claim 7, wherein Z$_2$ is

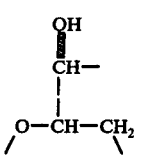

11. (5S)-5-Hydroxy-6α-PGI$_1$, a prostacyclin analog according to claim 10.

12. (5S)-5-Hydroxy-6α-PGI$_1$, methyl ester, a prostacyclin analog according to claim 10.

13. (5S)-5-Hydroxy-15-methyl-PGI$_1$, a prostacyclin analog according to claim 10.

14. (5S)-5-Hydroxy-16,16-dimethyl-PGI$_1$, a prostacyclin analog according to claim 10.

15. A prostacyclin analog according to claim 7, wherein Z$_2$ is

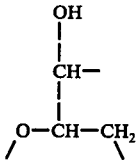

16. A prostacyclin analog according to claim 15, wherein Y$_1$ is cis—CH=CH—.

17. (5R)-5-Hydroxy-cis-13-6α-PGI$_1$, a prostacyclin analog according to claim 16.

18. A prostacyclin analog according to claim 5, wherein Y$_1$ is —C≡C—.

19. (5R)-5-Hydroxy-13,14-didehydro-6α-PGI$_1$, a prostacyclin analog according to claim 18.

20. A prostacyclin analog according to claim 15, wherein Y$_1$ is trans-CH=C(Hal)-.

21. (5R)-5-Hydroxy-14-chloro-6α-PGI$_1$, a prostacyclin analog according to claim 20.

22. A prostacyclin analog according to claim 15, wherein Y$_1$ is —CH$_2$CH$_2$—.

23. (5R)-5-Hydroxy-13,14-dihydro-6α-PGI$_1$, a prostacyclin analog according to claim 22.

24. A prostacyclin analog according to claim 15, wherein Y$_1$ is trans—CH=CH—.

25. A prostacyclin analog according to claim 24, wherein Z$_1$ is —(CH$_2$)$_g$—CH$_2$—CF$_2$.

26. 2,2-Difluoro-(5R)-5-hydroxy-6α-PGI$_1$, a prostacyclin analog according to claim 25.

27. A prostacyclin analog according to claim 24, wherein Z$_1$ is trans-(CH$_2$)$_g$—CH=CH—.

28. Trans-2,3-didehydro-(5R)-5-hydroxy-6α-PGI$_1$, a prostacyclin analog according to claim 27.

29. A prostacyclin analog according to claim 24, wherein Z$_1$ is —(CH$_2$)$_g$—CH$_2$—CH$_2$—.

30. A prostacyclin analog according to claim 27 wherein g is zero.

31. A prostacyclin analog according to claim 24, wherein R$_7$ is

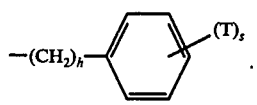

32. (5R)-5-Hydroxy-17-phenyl-18,19,20-trinor-6α-PGI$_1$, a prostacyclin analog according to claim 31.

33. A prostacyclin analog according to claim 30, wherein R$_7$ is

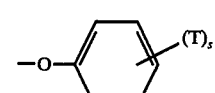

34. (5R)-5-Hydroxy-16-phenoxy-17,18,19,20-tetranor-6α-PGI$_1$, a prostacyclin analog according to claim 33.

35. A prostacyclin analog according to claim 30, wherein $R_7$ is $-(CH_2)_m-CH_3$.

36. A prostacyclin analog according to claim 35, wherein $X_6$ is $-COL_4$.

37. (5R)-5-Hydroxy-6α-PGI$_1$, amide, a prostacyclin analog according to claim 36.

38. A prostacyclin analog according to claim 35, wherein $X_6$ is $-CH_2OH$.

39. 2-Decarboxy-2-hydroxymethyl(5R)-5-hydroxy-6α-PGI$_1$, a prostacyclin analog according to claim 38.

40. A prostacyclin analog according to claim 35, wherein $X_6$ is $-COOR_1$.

41. A prostacyclin analog according to claim 40, wherein $R_5$ is methyl.

42. (5R)-5-hydroxy-15-methyl-6α-PGI$_1$, a prostacyclin analog according to claim 41.

43. A prostacyclin analog according to claim 40, wherein $R_5$ is hydrogen.

44. A prostacyclin analog according to claim 43, wherein at least one of $R_3$ and $R_4$ is fluoro.

45. (5R)-5-hydroxy-16,16-PGI$_1$, a prostacyclin analog according to claim 44.

46. A prostacyclin analog according to claim 43, wherein at least one of $R_3$ and $R_4$ is methyl.

47. (5R)-5-Hydroxy-16,16-dimethyl-6α-PGI$_1$, a prostacyclin analog according to claim 46.

48. A prostacyclin analog according to claim 43, wherein $R_3$ and $R_4$ are both hydrogen.

49. (5R)-5-Hydroxy-6α-PGI$_1$, methyl ester, a prostacyclin analog according to claim 48.

50. (5R)-5-Hydroxy-6α-PGI$_1$, tris(hydroxymethyl)-aminomethane salt, a prostacyclin analog according to claim 48.

51. (5R)-5-Hydroxy-6α-PGI$_1$, adamantanamine salt, a prostacyclin analog according to claim 48.

52. (5R)-5-hydroxy-6α-PGI$_1$, a prostacyclin analog according to claim 48.

* * * * *

UNITED STATES PATENT AND TRADEMARK OFFICE
CERTIFICATE OF CORRECTION

PATENT NO. : 4,110,532
DATED : August 29, 1978
INVENTOR(S) : Roy A. Johnson and John C. Sih It is certified that error appears in the above-identified patent and that said Letters Patent are hereby corrected as shown below:

Column 1, line 63, "6,9α-epoxy-5Z)" should read -- 6,9α-epoxy-(5Z) --;

Column 4, line 13, "-CH+CH-," should read -- -CH=CH-, --;

Column 10, line 10, "amido groups" should read -- amino groups --; line 12, "carbonylamido" should read -- carbonylamino --; line 17, "sulfonylamido" should read -- sulfonylamino --; line 20, "carbonylamido" should read -- carbonylamino --;

Column 15, line 64, "presen" should read -- present --;

Column 16, line 62, "provides and method" should read -- provides a method --;

Column 17, line 44, "employe" should read -- employed --; line 47, "metho" should read -- method --;

UNITED STATES PATENT AND TRADEMARK OFFICE
CERTIFICATE OF CORRECTION

PATENT NO. : 4,110,532
DATED : August 29, 1978
INVENTOR(S) : Roy A. Johnson and John C. Sih It is certified that error appears in the above-identified patent and that said Letters Patent are hereby corrected as shown below:

Column 23, line 2, "(5R)-6β-$PGI_1$" should read -- (5R)-5-hydroxy-6β-$PGI_1$ --;

Column 24, line 59, "5-hydroxy-6β" should read -- 5-hydroxy-6α --; line 62, "$PGF_2β$" should read -- $PGF_2α$ --; line 63, "$PGF_2β$" should read -- $PGF_2α$ --;

Column 31, line 15, "16-(m-trifluoromethylphenyl)" should read -- 16-(m-trifluoromethylphenoxy) --;

Column 33, line 10, two occurrences, "$PGL_1$" should read -- $PGI_1$ --;

Column 34, line 57, "amido" should read -- amino --; line 65, "carbonyl-amido" should read -- carbonylamino --; line 68, "sulphonylamide" should read -- sulfonylamido --;

Column 36, line 22, "according to claim 5," should read -- according to claim 15, --; line 47, "g is zero" should read -- g is one --;

Column 38, line 1, "16,16-$PGI_1$" should read -- 16,16-difluoro-6α-$PGI_1$ --.

Signed and Sealed this

Thirtieth Day of October 1979

[SEAL]

Attest:

RUTH C. MASON
Attesting Officer

LUTRELLE F. PARKER
Acting Commissioner of Patents and Trademarks